US009603996B2

(12) United States Patent
Grant et al.

(10) Patent No.: US 9,603,996 B2
(45) Date of Patent: Mar. 28, 2017

(54) SYSTEM AND METHOD FOR INSULIN PUMP MEDICAL DEVICE INCLUDING A SLIDER ASSEMBLY WHEREIN IMAGES ON DISPLAY ALLOW FOR HIGHLIGHTING AND MAGNIFYING IMAGES

(71) Applicant: DEKA Products Limited Partnership, Manchester, NH (US)

(72) Inventors: Kevin L. Grant, Litchfield, NH (US); Douglas J. Young, South Burlington, VT (US); Matthew C. Harris, Bow, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 14/852,900

(22) Filed: Sep. 14, 2015

(65) Prior Publication Data

US 2015/0374904 A1 Dec. 31, 2015

Related U.S. Application Data

(60) Division of application No. 13/405,670, filed on Feb. 27, 2012, now Pat. No. 9,134,823, which is a
(Continued)

(51) Int. Cl.
*G06F 3/00* (2006.01)
*A61M 5/142* (2006.01)
(Continued)

(52) U.S. Cl.
CPC ..... *A61M 5/14244* (2013.01); *G06F 3/03547* (2013.01); *G06F 3/0482* (2013.01); *G06F 3/04847* (2013.01); *G06F 19/3468* (2013.01); *G06K 9/2054* (2013.01); *G06Q 50/24* (2013.01); *G06T 3/40* (2013.01); *A61M 2005/14208* (2013.01); *A61M 2205/502* (2013.01); *A61M 2205/505* (2013.01); *A61M 2205/52* (2013.01);

(Continued)

(58) Field of Classification Search
CPC .................................................. G06F 3/03547
USPC ..... 710/1, 15, 18, 19, 62, 64, 72; 340/572.1, 340/5.2; 705/3; 715/733
See application file for complete search history.

(56) References Cited

U.S. PATENT DOCUMENTS

| | | | | | |
|---|---|---|---|---|---|
| 5,995,083 | A | * | 11/1999 | Sato ...................... | G06F 3/0488 178/18.01 |
| 6,790,178 | B1 | * | 9/2004 | Mault .................. | A61B 5/0011 128/903 |
| 7,821,503 | B2 | * | 10/2010 | Stephanick ........... | G06F 3/0236 178/18.01 |
| 8,009,014 | B2 | * | 8/2011 | Eberhart ................ | A61B 5/117 340/5.2 |
| 8,042,044 | B2 | * | 10/2011 | Van Leeuwen ..... | G06F 3/04842 345/157 |
| 8,346,399 | B2 | * | 1/2013 | Blomquist .......... | A61M 5/1452 604/118 |
| 8,400,417 | B2 | * | 3/2013 | Ording .................. | G06F 3/0488 345/173 |
| 9,134,823 | B2 | * | 9/2015 | Grant ................ | A61M 5/14244 |
| 2007/0233051 | A1 | * | 10/2007 | Hohl .................... | A61B 5/1486 604/891.1 |

(Continued)

*Primary Examiner* — Tammara Peyton
(74) *Attorney, Agent, or Firm* — McCormick, Paulding & Huber LLP

(57) ABSTRACT

A medical system includes an input assembly for receiving one or more user inputs. The input assembly includes at least one slider assembly for providing an input signal. Processing logic receives the input signal from the input assembly and provides a first output signal and a second output signal. A display assembly is configured to receive, at least in part, the first output signal from the processing logic and render information viewable by the user. The second output signal is provided to one or more medical system components. The information rendered on the display assembly may be manipulatable by the user and at least a portion of the information rendered may be magnified.

7 Claims, 7 Drawing Sheets

Related U.S. Application Data continuation of application No. 11/999,268, filed on Dec. 4, 2007, now Pat. No. 8,127,046.

(60) Provisional application No. 60/872,707, filed on Dec. 4, 2006.

(51) Int. Cl.
| | | |
|---|---|---|
| *G06F 3/0354* | (2013.01) | |
| *G06F 3/0482* | (2013.01) | |
| *G06Q 50/24* | (2012.01) | |
| *G06F 19/00* | (2011.01) | |
| *G06F 3/0484* | (2013.01) | |
| *G06K 9/20* | (2006.01) | |
| *G06T 3/40* | (2006.01) | |

(52) U.S. Cl.
CPC .............. *A61M 2230/201* (2013.01); *G06F 2203/0339* (2013.01)

(56) References Cited

U.S. PATENT DOCUMENTS

| | | | | |
|---|---|---|---|---|
| 2008/0055039 A1* | 3/2008 | Eberhart | ............... | A61B 5/117 340/5.2 |
| 2008/0076969 A1* | 3/2008 | Kraft | ................. | A61B 5/14532 600/300 |
| 2008/0178090 A1* | 7/2008 | Mahajan | .................. | G06F 1/16 715/733 |
| 2008/0198012 A1* | 8/2008 | Kamen | ............ | A61M 5/14244 340/572.1 |

\* cited by examiner

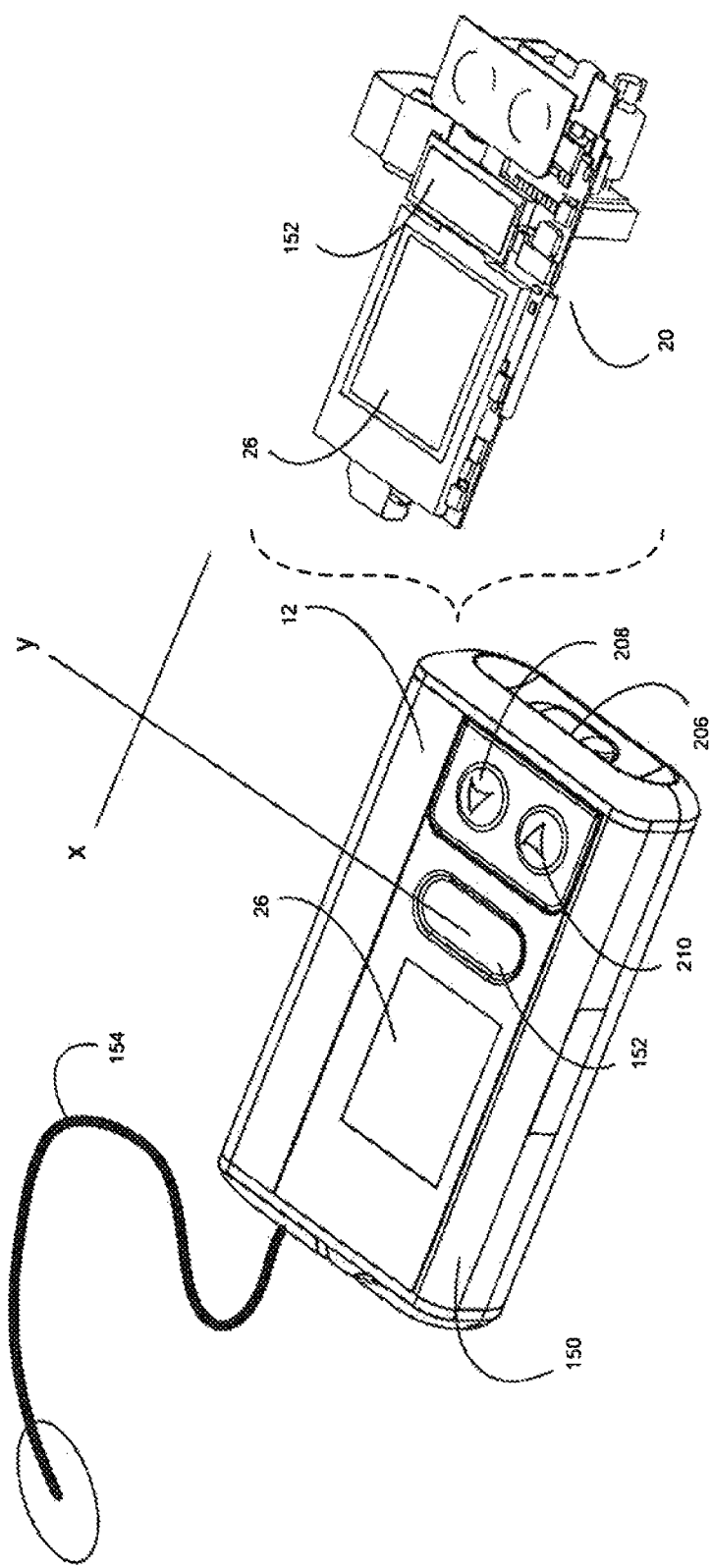

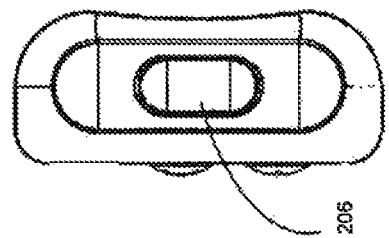
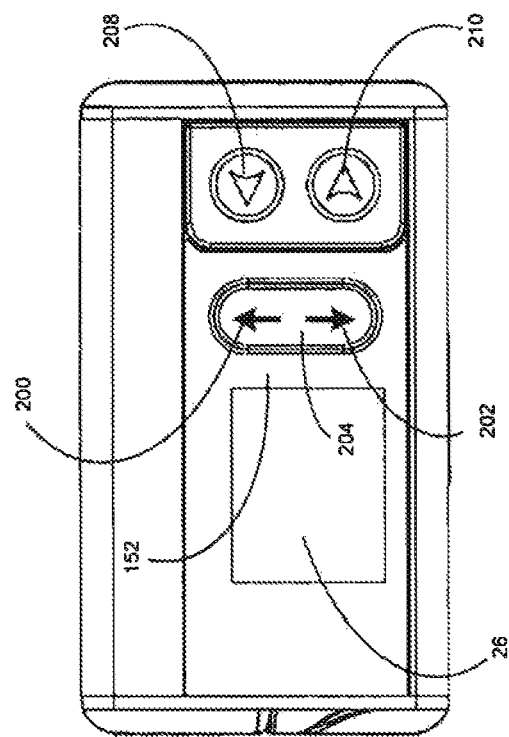
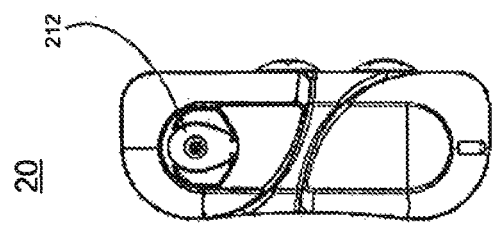

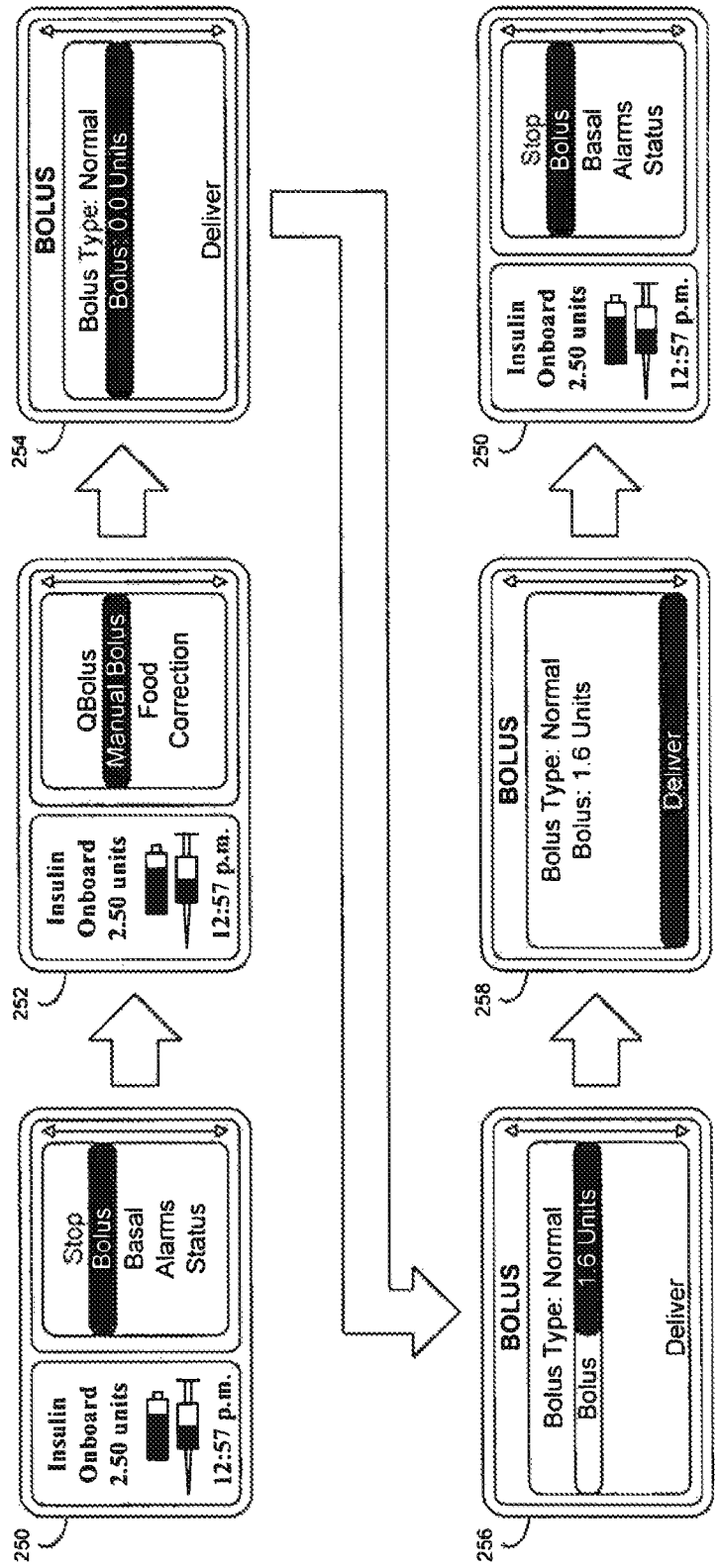

SYSTEM AND METHOD FOR INSULIN PUMP MEDICAL DEVICE INCLUDING A SLIDER ASSEMBLY WHEREIN IMAGES ON DISPLAY ALLOW FOR HIGHLIGHTING AND MAGNIFYING IMAGES

CROSS-REFERENCE TO RELATED APPLICATIONS

This application is a divisional of U.S. patent application Ser. No. 13/405,670, filed Feb. 27, 2012, which is a continuation of U.S. patent application Ser. No. 11/999,268, filed Dec. 4, 2007, which claims priority to U.S. Provisional Patent Application Ser. No. 60/872,707, filed Dec. 4, 2006, each of which is hereby incorporated by reference in its entirety.

TECHNICAL FIELD

This disclosure relates to slider assemblies and, more particularly, to medical devices that include slider assemblies.

BACKGROUND

Touch detectors have been in use to indicate a condition where there is contact between the touch detector and some other solid object (e.g., a finger). Any well-known electromechanical "on/off" switch may be used within a touch detector. Additionally, proximity detectors have also been used to indicate when one object is comparatively close to another object and, further, to measure how far away the object is from the detector.

"Capacitive" sensors may be used in proximity detectors and in touch detectors that require high reliability, as electromechanical switches may break or malfunction over time. A capacitive touch sensor may translate the capacitance of the capacitive sensor into a binary signal, which may be processed to determine whether the measured capacitance exceeds one or more defined capacitance levels. The effective capacitance measured may relate to the distance between the object (e.g., a finger) and a sensor plate. As is known in the art, capacitive sensors may use a dielectric material (e.g., polycarbonate) to cover the surface of the sensor plate and, therefore, separate the sensor plate and the object.

Unfortunately, medical devices often use input devices that have limited functionality. For example, medical devices may use binary switch assemblies that may require the user to repeatedly perform a task in order to achieve a desired goal. For example, the user may be required to repeatedly depress an "up arrow" switch in order to scroll "upward" through a menu. Alternatively, the user may be required to repeatedly depress a "down arrow" switch in order to scroll "downward" through the menu. The use of such limited functionality controls often make it difficult to use such a medical device.

SUMMARY OF DISCLOSURE

In a first implementation, a medical system includes an input assembly for receiving one or more user inputs. The input assembly includes at least one slider assembly for providing an input signal in response to the one or more user inputs. Processing logic receives the input signal from the input assembly and provides a first output signal and a second output signal. A display assembly is configured to receive, at least in part, the first output signal from the processing logic and render information viewable by the user. The second output signal is provided to one or more medical system components.

One or more of the following features may be included. The at least one slider assembly may be a capacitive slider assembly. The capacitive slider assembly may be configured, at least in part, to enable a user to manipulate the information rendered on the display assembly. Manipulating the information may include, at least in part, magnifying at least a portion of the information rendered on the display assembly. The medical system components may include a drug delivery mechanism.

The input assembly may include a selection confirmation assembly configured to generate a selection confirmation signal in response to a confirmatory user input. The selection confirmation assembly may be included within the at least one slider assembly. The input assembly may include an activation assembly configured to generate an activation signal in response to an activation input from the user.

A conductive housing may be electrically grounded to at least one of the input assembly, the display assembly, and the processing logic. The display assembly may be configured to scroll at least a portion of the information rendered on the display assembly. The at least one slider assembly may be configured to enable the user to regulate the rate at which the information is scrolled on the display assembly.

In another implementation, a medical system includes an input assembly for receiving one or more user inputs. The input assembly includes at least one capacitive slider assembly for providing an input signal in response to the one or more user inputs. Processing logic receives the input signal from the input assembly and provides a first output signal and a second output signal. A display assembly is configured to receive, at least in part, the first output signal from the processing logic and render information viewable by the user. The second output signal is provided to one or more medical system components. The medical system components include a drug delivery mechanism.

One or more of the following features may be included. The capacitive slider assembly may be configured, at least in part, to enable a user to magnify at least a portion of the information rendered on the display assembly. The input assembly may include a selection confirmation assembly configured to generate a selection confirmation signal in response to a confirmatory user input. The selection confirmation assembly may be included within the at least one slider assembly. The input assembly may include an activation assembly configured to generate an activation signal in response to an activation input from the user.

In another implementation, a method includes receiving an input signal in response to one or more user inputs from a user of a medical system that includes at least one slider assembly. The input signal is processed to generate a first output signal and a second output signal. Information that is viewable by the user is rendered on a display assembly. The information rendered is based at least in part upon the first output signal. The second output signal is provided to one or more medical system components.

One or more of the following features may be included. The information rendered on the display assembly may be manipulated. Manipulating the information may include magnifying at least a portion of the information rendered on the display assembly. A selection confirmation signal may be generated in response to a confirmatory user input. An activation signal may be generated in response to an activation input from the user. At least one of the input assembly, the display assembly, and the processing logic may be grounded to an electrically conductive housing.

The details of one or more implementations are set forth in the accompanying drawings and the description below. Other features and advantages will become apparent from the description, the drawings, and the claims.

BRIEF DESCRIPTION OF THE DRAWINGS

FIG. 3A is an isometric view of one embodiment of the medical system of FIG. 1;

FIG. 3B is an isometric view of one embodiment of the components of the medical system of FIG. 1;

FIG. 4 is a front elevation view of one embodiment of the medical system of FIG. 1;

FIG. 4L is a left-side elevation view of one embodiment of the medical system of FIG. 1;

FIG. 4R is a right-side elevation view of one embodiment of the medical system of FIG. 1;

FIGS. 5A-5F are illustrations of various menus rendered by the medical system of FIG. 1;

Like reference symbols in the various drawings indicate like elements.

DETAILED DESCRIPTION OF EXEMPLARY EMBODIMENTS

Figure 1:
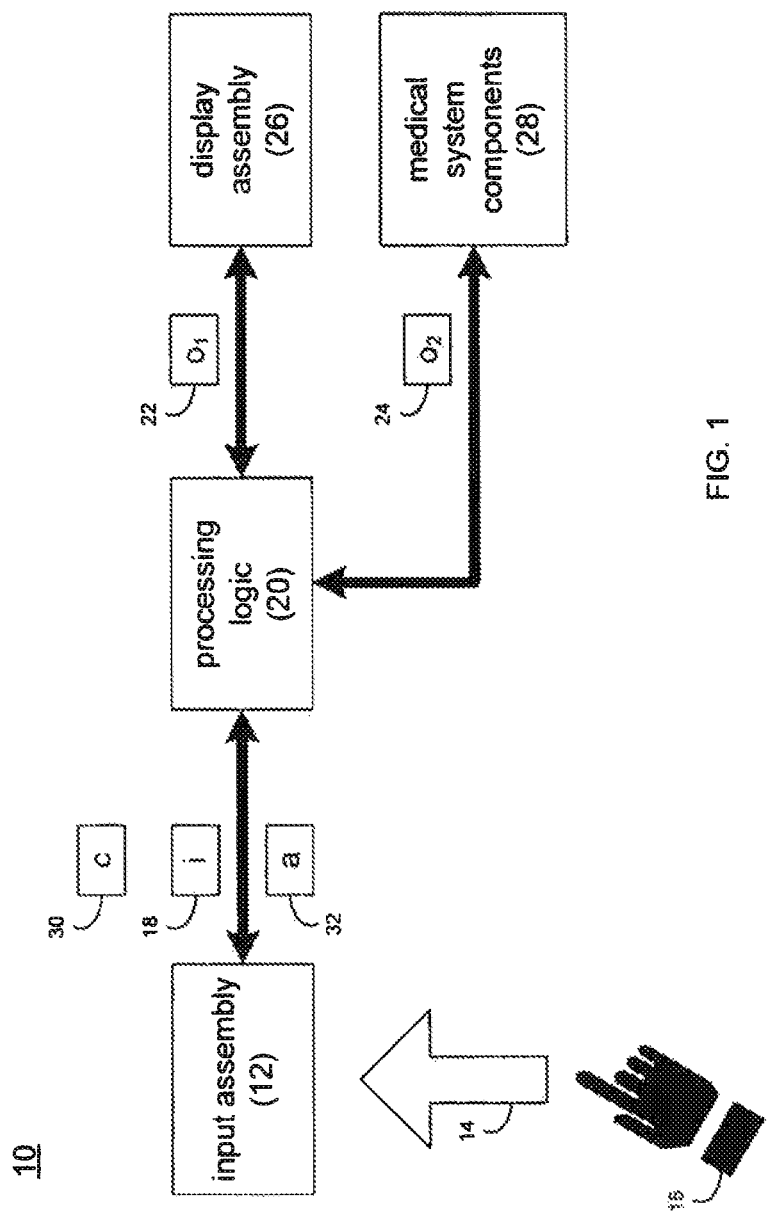
FIG. 1 is a diagrammatic view of a medical system.
Figure 2:
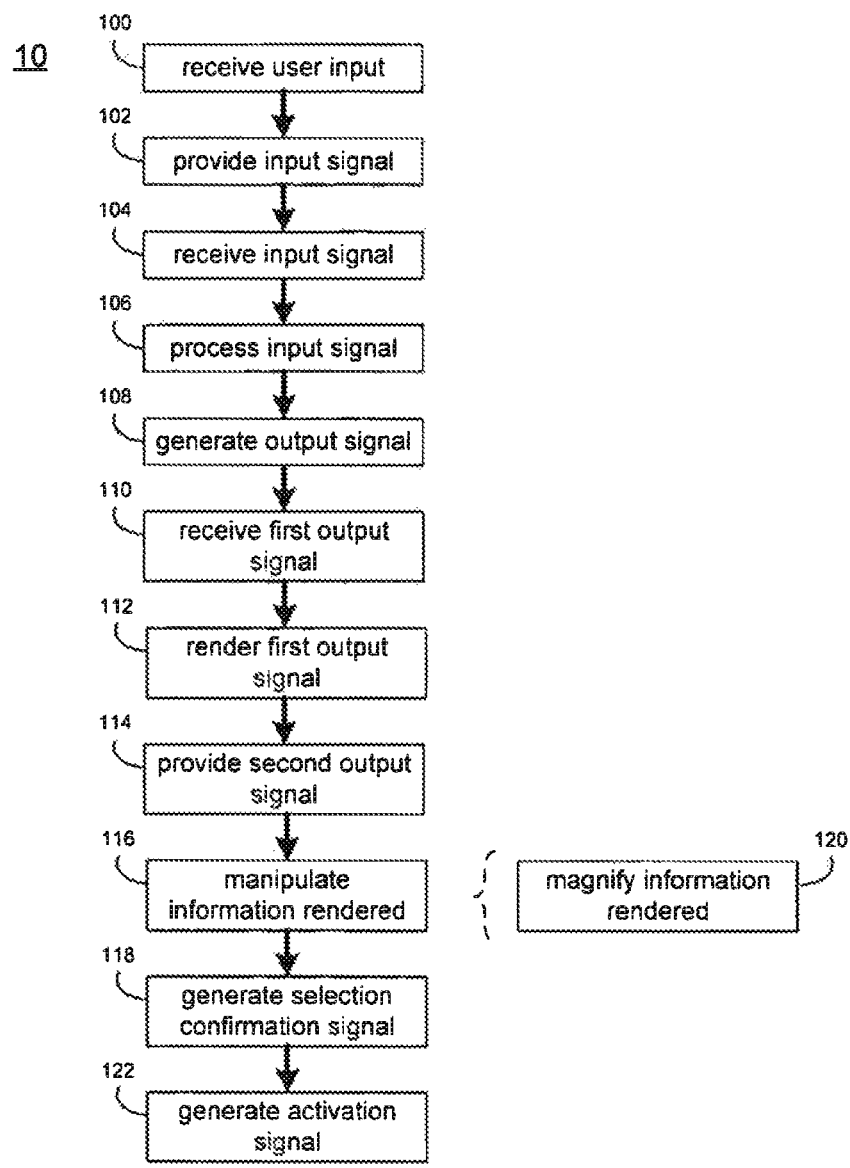
FIG. 2 is a flow chart of a process executed by the medical system of FIG. 1.

Referring to FIGS. 1 & 2, there is shown medical system 10. Examples of such medical systems may include but are not limited to various portable and non-portable medical devices, such as: drug delivery systems (e.g., insulin pumps), defibrillator systems, TENS (Transcutaneous Electrical Nerve Stimulator) systems, EMS (Electrical Muscle Stimulator) systems, glucose monitoring systems, and computerized medical monitoring systems.

While, as discussed above, medical system 10 may be any one of a plurality of various types of medical systems, for illustrative purposes, medical system 10 will be described in this disclosure as a drug delivery system. However, this is not intended to be a limitation of this disclosure and, accordingly, the following discussion may be equally applied to a variety of medical devices.

Medical system 10 may include at least one input assembly 12 for receiving 100 one or more user inputs 14 for one of more users 16 of medical system 10. For example, user 16 of medical device system 10 may manipulate input assembly 12 to provide the desired inputs. Examples of input assembly 12 may include but are not limited to one or more switch assemblies and one or more slider assemblies, each of which will be discussed below in greater detail. Accordingly, via input assembly 12, user 16 may provide one or more user inputs 14 that are received 100 by input assembly 12. Input assembly 12 may then provide 102 input signal 18 (responsive to one or more user inputs 14) to processing logic 20 of medical system 10.

Processing logic 20 may receive 104 input signal 18 from input assembly 12 and may process 106 input signal 18 to generate 108 one or more output signal. For example, processing logic 20 may generate 108 first output signal 22 and second output signal 24. First output signal 22 may be a display signal that is provided to display assembly 26 of medical system 10 and second output signal 24 may be a control signal that is provided to medical system components 28 of medical system 10.

Display assembly 26 may be configured to receive 110, at least in part, first output signal 22 from processing logic 20 and may render 112 visual information that is viewable by user 16 (to be discussed below in greater detail). Second output signal 24 may be provided 114 to one or more medical system components 26 included within medical system 10 (to be discussed below in greater detail).

As discussed above, for illustrative purposes, medical system 10 will be described in this disclosure as a drug delivery system. Accordingly, medical system components 28 may include various components of a drug delivery system, such as an insulin reservoir (not shown), an insulin pump assembly (not shown), various feedback systems (for ensuring that the proper insulin dosage was dispensed; not shown); and an infusion set (for delivering the insulin into the body; not shown).

Referring also to FIGS. 3A, 3B, 4, 4L & 4R, medical system 10 and the various components thereof (e.g. input assembly 12 processing logic 20 and display assembly 26) may be housed within a housing 150, that, in an exemplary embodiment, is a conductive housing 150 that may be electrically grounded to at least one of input assembly 12, processing logic 20, and display assembly 26, thus shielding the various components included within medical system 10 from e.g. external noise sources. Conductive housing 150 may be constructed of an electrically conductive material such as e.g. aluminum, copper, tin, brass, bronze and electrically conductive plastic, such as conductive polymers and thermoplastics. In other embodiments, the housing 150 may be made of any non-conductive materials, e.g., plastic.

Input assembly 12 may include at least one slider assembly 152 for allowing user 16 to manipulate the information rendered on display assembly 26. For example and as will be discussed below in greater detail, slider assembly 152 may allow user 16 to scroll through various menu items rendered on display assembly 26. While slider assembly 152 is shown to allow for movement along a single axis (e.g. the y-axis), this is for illustrative purposes only and is not intended to be a limitation of this disclosure. Specifically, slider assembly 152 may be configured to allow for multi-axial movement along one or more additional axes, such as the x-axis axis.

An example of slider assembly 152 may include a capacitive slider assembly, which may be implemented using a CY8C21434-24LFXI PSOC offered by Cypress Semiconductor of San Jose, Calif., the design and operation of which are described within the "CSD User Module" published by Cypress Semiconductor and attached hereto as Appendix A.

If slider assembly 152 is configured as a capacitive slider assembly, slider assembly 152 may include a combination of e.g., capacitive assemblies and oscillator circuits for charging the capacitive assemblies. Decision logic (included within input assembly 12 and/or processing logic 20) may provide compensation for environmental factors (e.g., temperature, humidity, and power supply voltage change). In most capacitive slider assembly applications, the capacitive slider assembly includes an insulation overlay (not shown) that covers a sensing electrode (not shown). The thickness and the dielectric constant value of the insulation overlay may determine the inter-capacitance between the sensing electrode and e.g., a human finger.

As is known in that art, as a user (e.g., user 16) moves their finger along the length of slider assembly 152, if configured as a capacitive slider assembly, the capacitance of slider assembly 152 may vary. This varying capacitance may be used to generate input signal 18 provided to processing logic 20. For example, circuitry included within input assembly 12 may generate a digital representation of the capacitance of slider assembly 152, which may be provided to processing logic 20 as input signal 18.

Referring also to FIG. 5A, slider assembly 152 may be configured, at least in part, to enable user 16 to manipulate 116 the information rendered 112 on display assembly 26. For example, via slider assembly 152, user 16 may slide their finger in the direction of arrow 200, resulting in the highlighted portion of the information included within main menu 250 (shown in FIG. 5A) rendered on display assembly 26 scrolling upward. Alternatively, user 16 may slide their finger in the direction of arrow 202, resulting in the highlighted portion of the information included within main menu 250 rendered on display assembly 26 scrolling downward.

Accordingly, user 16 may slide their finger upward (in the direction of arrow 200) and the highlighted portion of main menu 250 may change from "Bolus" to "Stop". Therefore, when user 16 slides their finger upward, input assembly 12 receives 100 user input 14 from user 16. Slider assembly 152 may process user input 14 and generate a "scroll upward" input signal 18 that may be provided 102 to processing logic 20. Upon receiving 104 "scroll upward" input signal 18, processing logic 20 may process 106 "scroll upward" input signal 18 and generate 108 first output signal 22 that is provided to display assembly 26. Upon receiving 110 first output signal 22, display assembly 26 may process first output signal 22 and may scroll the highlighted portion of main menu 250 upward so that "Stop" is highlighted.

Further, user 16 may slide their finger downward (in the direction of arrow 202) and the highlighted portion of main menu 250 may change from "Bolus" to "Basal". Therefore, when user 16 slides their finger downward, input assembly 12 receives 100 user input 14 from user 16. Slider assembly 152 may process user input 14 and generate a "scroll downward" input signal 18 that may be provided 102 to processing logic 20. Upon receiving 104 "scroll downward" input signal 18, processing logic 20 may process 106 "scroll downward" input signal 18 and generate 108 first output signal 22 that is provided to display assembly 26. Upon receiving 110 first output signal 22, display assembly 26 may process first output signal 22 and may scroll the highlighted portion of main menu 250 downward so that "Basal" is highlighted.

As discussed above, if configured as a capacitive slider assembly, the capacitance of slider assembly 152 may vary depending on the position of the finger of user 16 with respect to slider assembly 152. Accordingly, slider assembly 152 may be configured so that a capacitance is generated that is indicative of the displacement of the finger of user 16 with respect to point of origin 204. For example, the "upward" portion of slider assembly 152 may be configured to provide e.g. four discrete and unique capacitance readings that vary depending upon the "upward" displacement of the finger of user 16 with respect to point of origin 204. Further, the "downward" portion of slider assembly 152 may be configured to provide e.g. four discrete and unique capacitance readings that vary depending upon the "downward" displacement of the finger of user 16 with respect to point of origin 204. While the granularity of slider assembly 152 is described above as having a point of origin, four "upward" capacitance values and four "downward" capacitance values, this is for illustrative purposes only and is not intended to be a limitation of this disclosure, as the number of "upward" and "downward" capacitance values, as well as the point of origin, may vary depending upon e.g. design criteria and system requirements.

Accordingly, slider assembly 152 may be configured so that the rate at which e.g. the highlighted portion of main menu 250 scrolls "upward" or "downward" varies depending upon the displacement of the finger of user 16 with respect to point of origin 204. Therefore, if user 16 wishes to quickly scroll "upward", user 16 may position their finger near the top of slider assembly 152. Likewise, if user 16 wishes to quickly scroll "downward", user 16 may position their finger near the bottom of slider assembly 152. Additionally, if user 16 wishes to slowly scroll "upward", user 16 may position their finger slightly "upward" with respect to point of origin 204. Further, if user 16 wishes to slowly scroll "downward", user 16 may position their finger slightly "downward" with respect to point of origin 204.

Once the appropriate menu item is highlighted, user 16 may select the highlighted menu item via input assembly 12. In order to facilitate such a selection, input assembly 12 may include a selection confirmation assembly configured to generate 118 selection confirmation signal 30 in response to a confirmatory user input (to be discussed below in greater detail). For example, input assembly 12 may include one or more switch assemblies 206, 208, 210 (e.g., selection confirmation assemblies) for allowing user 16 to e.g. select menu items, place medical system 10 into sleep mode, and awake medical system 10 from sleep mode, which examples are not meant to be limitations of this disclosure, as the one or more switch assemblies 206, 208, 210 may be programmed to impart any function.

Referring also to FIGS. 5B-5F, assume for illustrative purposes that medical system 10 is an insulin pump and user 14 wishes to configure a 1.6 unit bolus dose of insulin. Accordingly, user 14 may use slider assembly 152 to highlight "Bolus" within main menu 250 rendered on display assembly 26. User 14 may then use switch assembly 210 to select "Bolus". Once selected, selection confirmation signal 30 may be generated 118 and provided to processing logic 20. Processing logic 20 may then provide the appropriate signals to display assembly 26 so that submenu 252 may be rendered (as shown in FIG. 5B).

User 14 may then use slider assembly 152 to highlight "Manual Bolus" within submenu 252, which may be selected using switch assembly 210 to generate selection confirmation signal 30, which may be provided to processing logic 20. Processing logic 20 may then provide the appropriate signal to display assembly 26 so that submenu 254 may be rendered (as shown in FIG. 5C).

User 14 may then use slider assembly 152 to highlight "Bolus: 0.0 Units" within submenu 254, which may be selected using switch assembly 210 to generate selection confirmation signal 30, which may be provided to processing logic 20. Processing logic 20 may then provide the appropriate signal to display assembly 26 so that submenu 256 may be rendered (as shown in FIG. 5D).

User 14 may then use slider assembly 152 to adjust the "Bolus" insulin amount to "1.6 units", which may be selected using switch assembly 210 to generate selection confirmation signal 30, which may be provided to processing logic 20. Processing logic 20 may then provide the appropriate signal to display assembly 26 so that confirmation menu 258 may be rendered (as shown in FIG. 5E).

User 14 may then use slider assembly 152 to highlight "Deliver", which may be selected using switch assembly 210 to generate selection confirmation signal 30, which may be provided to processing logic 20. Processing logic 20 may then provide 114 second output signal 24 to one or more medical system components 26 included within medical system 10, resulting in the injection of e.g., 1.6 units of insulin through e.g., infusion set 154 (See FIG. 3) coupled to infusion port 212 (See FIG. 4L).

As discussed above, for illustrative purposes, assume that medical system 10 is an insulin pump. Accordingly, medical system 10 may include an insulin reservoir (not shown), a pumping assembly (not shown), various feedback systems (for ensuring that the proper insulin dosage was dispensed; not shown), and infusion set 154 (for delivering the insulin into the body; See FIG. 3A). Accordingly, second output signal 24 may be provided to medical system components 26, which may process second output signal 24 and effectuate the injection of e.g., 1.6 units of insulin.

Once the appropriate insulin dose is delivered, processing logic 20 may then provide the appropriate signal to display assembly 26 so that main menu 250 may once again be rendered (as shown in FIG. 5F).

While medical system 10 is described above as requiring user 16 to select menu items via switch assembly 210 (thus generating 118 selection confirmation signal 30), this is for illustrative purposes only and is not intended to be a limitation of this disclosure. For example, switch assembly 206 or switch assembly 208 may be utilized to select the highlighted menu item and generate 118 selection confirmation signal 30. Alternatively, slider assembly 152 may be configured to allow user 16 to select a highlighted menu item and generate 118 selection confirmation signal 30. For example, slider assembly 152 may be configured so that if user 16 positions their finger at point of origin 204 for longer than a defined period of time (e.g. three seconds), the highlighted menu item may be selected and selection confirmation signal 30 may be generated 118.

Figure 6:
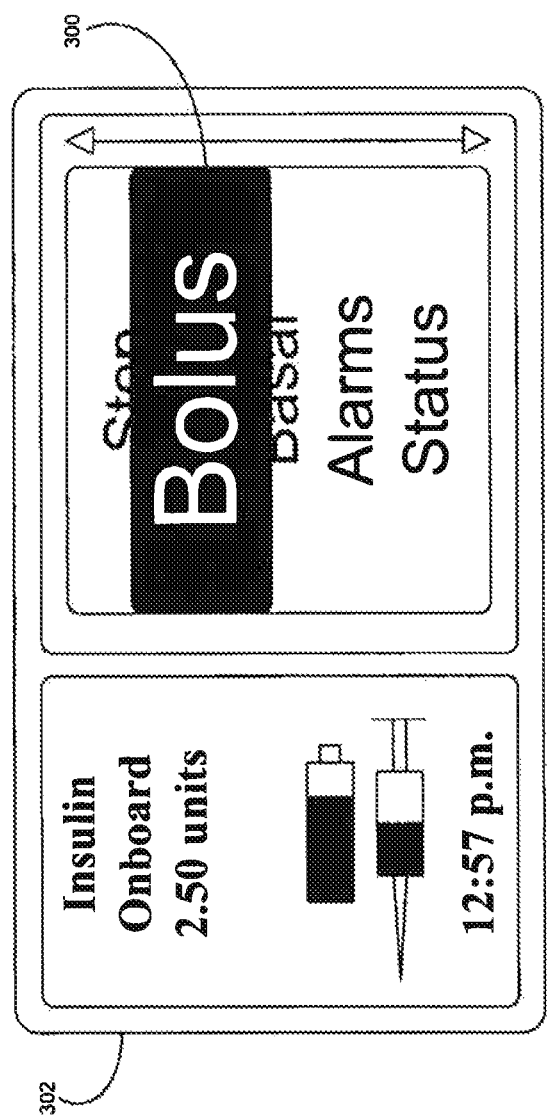
FIG. 6 is an illustration of another view of a menu rendered by the medical system of FIG. 1.

Manipulating 116 the information rendered 112 on display assembly 26 may include, at least in part, magnifying 120 at least a portion of the information rendered 112 on display assembly 26. For example and referring also to FIG. 6, when a portion of a menu is highlighted, the highlighted portion may be magnified 120 with respect to the unmagnified portion. Accordingly, highlighted portion 300 (i.e., "Bolus") may be magnified 120 by medical system 10 so that it may be easier to read by user 16. While magnification 120 of highlighted portion 300 may result in adjacent menu items (e.g. "Basal" and "Stop") being partially obscured, in the event that user 16 uses slider assembly 152 to scroll highlighted portion 300 "upward" or "downward", the partially obscured menu items will be unobscured and magnified 120.

Medical system 10 may be configured so that the system 10 enters into a "sleep" mode after a defined period of time. "Sleep" mode may be configured to allow medical system 10 to conserve electrical power while in "sleep" mode. Accordingly, display assembly 26 may dim or go blank. Once in "sleep" mode, medical system 10 may be configured to allow the user to "wake" medical system 10 from "sleep" mode.

Medical system 10 may be configured to automatically enter into "sleep" mode after a defined period of time in which medical system 10 does not receive an input signal (e.g. input signal 18) from user 16. For example, medical system 10 may be configured so that if an input signal is not received for a period of three minutes, medical system 10 may automatically enter "sleep" mode. Alternatively/additionally, medical system 10 may be configured so that user 16 may initiate "sleep" mode. For example, medical system 10 may be configured so that if user 16 depresses switch assembly 210 for greater than a defined period of time (e.g. three seconds), processing logic 20 may execute the appropriate sequence of steps to place medical system 10 into "sleep" mode. This embodiment is not limited to the use of switch assembly 210, in other embodiments; switch assembly 208 or 206 may be used. In still other embodiments, slider assembly 152 may be used to enter into "sleep" mode.

In order to facilitate exiting from "sleep" mode, input assembly 12 may include an activation assembly configured to generate 122 activation signal 32 in response to an activation input (to be discussed below in greater detail) from user 16. For example, medical system 10 may be configured so that, when in "sleep" mode, if user 16 depresses switch assembly 206 for greater than a defined period of time (e.g. three seconds), activation signal 32 may be generated 122 and provided to processing logic 20. Upon receiving activation signal 32, processing logic 20 may execute the appropriate sequence of steps to awake medical system 10 from "sleep" mode.

While slider assembly 152 is described above as being a capacitive slider assembly, this is for illustrative purposes only and is not intended to be a limitation of this disclosure. For example, slider assembly 152 may be a resistive slider assembly.

Figure 7:
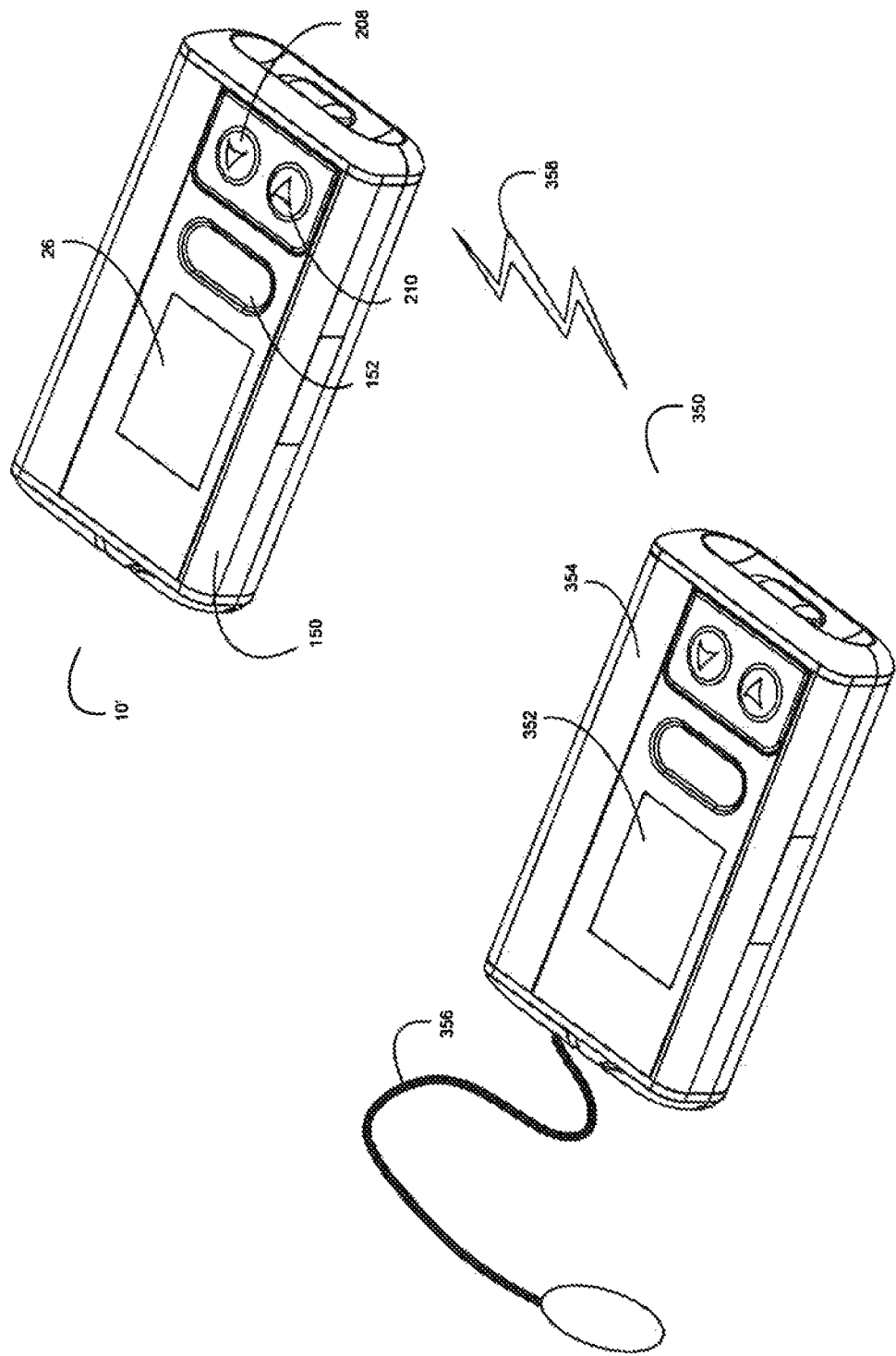
FIG. 7 is an isometric view of an alternative embodiment of the medical system of FIG. 1.

Additionally and referring also to FIG. 7, in one exemplary embodiment of the above-described medical system, medical system 10' may be used to communicate with a remote medical system (e.g., remote medical system 350). In this particular embodiment, medical system 10' may include telemetry circuitry (not shown) that allows for communication (e.g., wired or wireless) between medical system 10' and e.g., remote medical system 350, thus allowing medical system 10' to remotely control remote medical system 350. Remote medical system 350, which may also include telemetry circuitry (not shown) and may be capable of communicating with medical system 10', may be configured similarly to that of medical system 10' and, therefore, may include display assembly 352, input assembly 354, and processing logic (not shown). Additionally, remote medical system 350 may include medical system components (not shown), examples of which may include but are not limited to various components of a drug delivery system e.g., an insulin reservoir (not shown), an insulin pump assembly (not shown), various feedback systems (for ensuring that the proper insulin dosage was dispensed; not shown); and infusion set 356 (for delivering the insulin into the body).

In this particular embodiment, processing logic within medical system 10' may be configured to send the above-described first output signal (i.e., first output signal 22 as shown in FIG. 1) to display assembly 26 included within medical system 10' and also to display assembly 352 included within remote medical system 350 (via communication channel 358 established between medical system 10' and remote medical system 350). As discussed above, communication channel 358 may be a wired or wireless communication channel. Alternatively, medical system 10' may not include a display assembly and, therefore, the above-described first output signal (i.e., first output signal 22 as shown in FIG. 1) may only be provided to display assembly 352 included within remote medical system 350 (via communication channel 358).

Additionally and as discussed above, remote medical system 350 may include medical system components (not shown). Accordingly, when medical system 10' provides the above-described second output signal (i.e., second output signal 24 as shown in FIG. 1), the second output signal may be provided (via communication channel 358) to the medical system components (not shown) included within remote medical system 350 instead of (or in addition to) the medical system components (e.g., medical system components 28 of FIG. 1) included within medical system 10'. For example, the medical system components included within medical system 10' may include a continuous glucose monitor (not shown) or a glucose meter (not shown). Accordingly, a second output signal may be provided to the continuous glucose monitor, instructing the continuous glucose monitor to take a glucose measurement and the resulting measurement data may be provided (via communication channel 358) to remote medical system 350, which may process this measurement data and provide an output signal to the medical system components included within remote medical system 350.

A number of implementations have been described. Nevertheless, it will be understood that various modifications may be made. Accordingly, other implementations are within the scope of the following claims.

What is claimed is:

1. A medical system comprising:
   a first medical device comprising:
   a reservoir for holding a fluid;
   a pump assembly for pumping fluid out of the reservoir for delivery;
   a feedback system for indicating the dosage of fluid delivered;
   a display assembly for rendering information;
   an input assembly comprising at least one slider assembly, for manipulating the information rendered on the display assembly and for providing an input signal in response to an input; and
   a computer program product residing on a computer readable medium having a plurality of instructions stored thereon which, when executed by a processor, cause the processor to perform operations comprising:
   selecting information on the display assembly; and
   simultaneously highlighting and magnifying the selected information on the display assembly with respect to nonhighlighted information on the display without changing a location on the display relative to the nonhighlighted information at which the simultaneously highlighted and magnified portion of the information is displayed.

2. The system of claim 1 wherein the slider assembly is a capacitive slider assembly.

3. The system of claim 2 wherein the input assembly comprising decision logic configured to provide compensation to the input signal for at least one environmental factor.

4. The system of claim 1 wherein the slider assembly is configured to allow multi-axial movement.

5. The system of claim 1 wherein the system further comprising a second medical device for communicating with the first medical device, the second medical device comprising:
   telemetry circuitry for communication with the first medical device;
   a display assembly for rendering information; and
   an input assembly comprising at least one slider assembly for manipulating the information rendered on the display assembly and for providing an input signal in response to an input.

6. The system of claim 5 wherein the medical device further comprising a glucose meter.

7. The system of claim 5 wherein the medical device further comprising a continuous glucose monitor.

* * * * *